United States Patent
Kudo

(10) Patent No.: US 10,799,339 B2
(45) Date of Patent: Oct. 13, 2020

(54) INTRAOCULAR LENS INJECTOR

(71) Applicant: Hoya Corporation, Tokyo (JP)

(72) Inventor: Kazunori Kudo, Saku (JP)

(73) Assignee: Hoya Corporation, Tokyo (JP)

( * ) Notice: Subject to any disclaimer, the term of this patent is extended or adjusted under 35 U.S.C. 154(b) by 269 days.

(21) Appl. No.: 15/756,569

(22) PCT Filed: Sep. 15, 2016

(86) PCT No.: PCT/JP2016/077328
§ 371 (c)(1),
(2) Date: Aug. 12, 2018

(87) PCT Pub. No.: WO2017/047715
PCT Pub. Date: Mar. 23, 2017

(65) Prior Publication Data
US 2018/0353287 A1    Dec. 13, 2018

(30) Foreign Application Priority Data

Sep. 16, 2015    (JP) .................. 2015-182569

(51) Int. Cl.
*A61F 2/14*    (2006.01)
*A61F 2/16*    (2006.01)

(52) U.S. Cl.
CPC .............. *A61F 2/167* (2013.01); *A61F 2/16* (2013.01); *A61F 2002/1683* (2013.01)

(58) Field of Classification Search
CPC .......... A61F 2/167; A61F 2/16; A61F 2/1672; A61F 2/1667; A61F 2/1662;
(Continued)

(56) References Cited

U.S. PATENT DOCUMENTS 2,761,446 A    9/1956    Reed
3,212,685 A    10/1965    Swan
(Continued)

FOREIGN PATENT DOCUMENTS

DE    3610925    10/1987
DE    4110278    10/1992
(Continued)

OTHER PUBLICATIONS

U.S. Appl. No. 15/063,395, filed Mar. 7, 2016, US 20160346077A1.
(Continued)

*Primary Examiner* — Erich G Herbermann
(74) *Attorney, Agent, or Firm* — Henricks Slavin LLP

(57) ABSTRACT

There is provided an intraocular lens injector configured to inject an intraocular lens 7 having an optical portion 8 and a pair of support portions 9a, 9b extending from the optical portion 8 into an eye, including: an injector main body 2 having a lens setting portion 6 on which the intraocular lens 7 is set; a holding portion 14 that holds a tip end part of a front support portion 9a of the pair of support portions 9a, 9b, which is disposed in front of the lens setting portion 6; and a guide mechanism (11c, 14a) that guides the optical portion 8 to pass under the holding portion 14 when the intraocular lens 7 is pushed out by the pushing member 5 so that the optical portion 8 is displaced downward relatively to the front support portion 9a held by the holding portion 14.

13 Claims, 9 Drawing Sheets

(58) Field of Classification Search
CPC .... A61F 2002/1683; A61F 2002/1681; A61M 5/3205; A61M 5/20; A61M 5/178; A61M 5/30; A61M 5/14; A61M 3/00
See application file for complete search history.

(56) References Cited

U.S. PATENT DOCUMENTS

| | | | |
|---|---|---|---|
| 4,205,747 A | 6/1980 | Gilliam et al. |
| 4,269,307 A | 5/1981 | LaHaye |
| 4,423,809 A | 1/1984 | Mazzocco |
| 4,573,998 A | 3/1986 | Mazzocco |
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,810,249 A | 3/1989 | Haber et al. |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,259,395 A | 11/1993 | Li |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,645,534 A | 7/1997 | Chanoch |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A | 3/1998 | Levander |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold et al. |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 5,957,896 A | 9/1999 | Bendek et al. |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,050,999 A | 4/2000 | Paraschac et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,506,195 B2 | 1/2003 | Chambers et al. |
| 6,537,283 B2 | 3/2003 | Van Noy |
| 6,540,754 B2 | 4/2003 | Brady |

(56) References Cited

U.S. PATENT DOCUMENTS

| | | |
|---|---|---|
| 6,554,839 B2 | 4/2003 | Brady |
| 6,558,395 B2 | 5/2003 | Hjertman et al. |
| 6,605,093 B1 | 8/2003 | Blake |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,793,674 B2 | 9/2004 | Zapata |
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,526 B2 | 7/2013 | Pynson |
| 8,475,528 B2 | 7/2013 | Ichinohe et al. |
| 8,523,877 B2 | 9/2013 | Ichinohe et al. |
| 8,523,941 B2 | 9/2013 | Ichinohe et al. |
| 8,535,375 B2 | 9/2013 | Ichinohe et al. |
| 8,545,512 B2 | 10/2013 | Ichinohe et al. |
| 8,574,239 B2 | 11/2013 | Ichinohe et al. |
| 8,603,103 B2 | 12/2013 | Kudo et al. |
| 8,647,382 B2 | 2/2014 | Kudo et al. |
| 8,702,795 B2 | 4/2014 | Shoji et al. |
| 8,747,465 B2 | 6/2014 | Someya et al. |
| 8,968,328 B2 | 3/2015 | Ichinohe et al. |
| 9,114,006 B2 | 8/2015 | Inoue |
| 9,114,007 B2 | 8/2015 | Ichinohe et al. |
| 9,186,246 B2 | 11/2015 | Inoue |
| 9,220,593 B2 | 12/2015 | Ichinohe |
| 9,289,288 B2 | 3/2016 | Someya et al. |
| 9,314,373 B2 | 4/2016 | Kudo et al. |
| 9,326,847 B2 | 5/2016 | Sanger |
| 9,364,320 B2 | 6/2016 | Ichinohe et al. |
| 9,554,894 B2 | 1/2017 | Inoue |
| 9,572,710 B1 | 2/2017 | Kudo et al. |
| 9,655,718 B2 | 5/2017 | Kudo |
| 9,687,340 B2 | 6/2017 | Anderson |
| 9,877,826 B2 | 1/2018 | Kudo et al. |
| 9,901,442 B2 | 2/2018 | Kudo et al. |
| 9,907,647 B2 | 3/2018 | Inoue |
| 9,998,081 B2 | 5/2018 | Kudo et al. |
| 10,039,668 B2 | 8/2018 | Kudo et al. |
| 10,383,723 B2 | 8/2019 | Kudo |
| 10,390,940 B2 | 8/2019 | Someya et al. |
| 10,405,971 B2 | 9/2019 | Someya et al. |
| 10,517,717 B2 | 12/2019 | Inoue |
| 2001/0007942 A1 | 7/2001 | Kikuchi et al. |
| 2002/0103490 A1 | 8/2002 | Brady |
| 2002/0151904 A1 | 10/2002 | Feingold et al. |
| 2002/0165610 A1 | 11/2002 | Waldock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050647 A1 | 3/2003 | Brady |
| 2003/0088253 A1 | 5/2003 | Seil |
| 2003/0139749 A1 | 7/2003 | Kikuchi et al. |
| 2003/0181921 A1 | 9/2003 | Jeannin |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212408 A1 | 11/2003 | Kobayashi |
| 2003/0212409 A1 | 11/2003 | Kobayashi et al. |
| 2004/0111094 A1 | 6/2004 | Meyer |
| 2004/0117012 A1 | 6/2004 | Vincent |
| 2004/0127911 A1 | 7/2004 | Figueroa |
| 2004/0147938 A1 | 7/2004 | Dusek et al. |
| 2004/0186428 A1 | 9/2004 | Ray |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero et al. |
| 2005/0055011 A1 | 3/2005 | Enggaard |
| 2005/0125000 A1 | 6/2005 | Tourrette et al. |
| 2005/0143750 A1 | 6/2005 | Vaquero |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1 | 4/2006 | Dusek |
| 2006/0142781 A1 | 6/2006 | Pynson et al. |
| 2006/0167466 A1 | 7/2006 | Dusek |
| 2006/0200167 A1 | 9/2006 | Peterson et al. |
| 2006/0229633 A1 | 10/2006 | Shepherd |
| 2006/0235429 A1 | 10/2006 | Lee et al. |
| 2006/0293694 A1 | 12/2006 | Futamura |
| 2007/0005135 A1 | 1/2007 | Makker et al. |
| 2007/0270945 A1 | 11/2007 | Kobayashi |
| 2008/0033449 A1 | 2/2008 | Cole et al. |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0036898 A1 | 2/2009 | Ichinohe |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 | 8/2009 | Ichinohe et al. |
| 2009/0216244 A1 | 8/2009 | Pynson |
| 2009/0248031 A1 | 10/2009 | Ichinohe |
| 2009/0270876 A1 | 10/2009 | Hoffmann et al. |
| 2009/0292293 A1 | 11/2009 | Bogaert et al. |
| 2010/0094309 A1 | 4/2010 | Hboukhny et al. |
| 2010/0106160 A1 | 4/2010 | Tsai |
| 2010/0161049 A1 | 6/2010 | Inoue |
| 2010/0185206 A1 | 7/2010 | Ichinohe et al. |
| 2010/0217273 A1 | 8/2010 | Someya et al. |
| 2010/0286704 A1 | 11/2010 | Ichinohe et al. |
| 2010/0331808 A1 | 12/2010 | Py et al. |
| 2011/0046633 A1 | 2/2011 | Pankin et al. |
| 2011/0046635 A1 | 2/2011 | Pankin et al. |
| 2011/0082463 A1 | 4/2011 | Inoue |
| 2011/0098717 A1 | 4/2011 | Inoue |
| 2011/0144654 A1 | 6/2011 | Isaacs et al. |
| 2011/0172676 A1 | 7/2011 | Chen |
| 2011/0264101 A1 | 10/2011 | Inoue et al. |
| 2011/0270264 A1 | 11/2011 | Shoji et al. |
| 2011/0288557 A1 | 11/2011 | Kudo et al. |
| 2012/0022548 A1 | 1/2012 | Zacharias |
| 2012/0022549 A1 | 1/2012 | Someya et al. |
| 2012/0071887 A1 | 3/2012 | Ichinohe et al. |
| 2012/0123438 A1 | 5/2012 | Horvath et al. |
| 2013/0006259 A1 | 1/2013 | Sanger |
| 2013/0018460 A1 | 1/2013 | Anderson |
| 2013/0085507 A1 | 4/2013 | Nagasaka |
| 2013/0226193 A1* | 8/2013 | Kudo ................. A61F 2/148 606/107 |
| 2013/0245635 A1 | 9/2013 | Inoue |
| 2013/0345713 A1 | 12/2013 | Cole et al. |
| 2014/0081284 A1 | 3/2014 | Ichinohe et al. |
| 2014/0107660 A1 | 4/2014 | Ichinohe et al. |
| 2014/0114323 A1 | 4/2014 | Kudo et al. |

(56) References Cited

U.S. PATENT DOCUMENTS

| | | |
|---|---|---|
| 2014/0135784 A1 | 5/2014 | Maroscheck |
| 2014/0180299 A1 | 6/2014 | Ichinohe et al. |
| 2014/0180300 A1 | 6/2014 | Ichinohe et al. |
| 2014/0194890 A1 | 7/2014 | Kudo et al. |
| 2014/0276901 A1 | 9/2014 | Auld |
| 2015/0327992 A1 | 11/2015 | Wagner et al. |
| 2016/0000556 A1 | 1/2016 | Perera |
| 2016/0113759 A1 | 4/2016 | Inoue |
| 2016/0151150 A1 | 6/2016 | Sato |
| 2016/0193038 A1 | 7/2016 | Kudo et al. |
| 2016/0256316 A1 | 9/2016 | Van Noy et al. |
| 2016/0270907 A1 | 9/2016 | Attinger |
| 2016/0331587 A1 | 11/2016 | Yamada et al. |
| 2016/0346077 A1 | 12/2016 | Someya et al. |
| 2017/0079772 A1 | 3/2017 | Kudo |
| 2017/0151056 A1 | 6/2017 | Inoue |
| 2017/0202662 A1 | 7/2017 | Someya et al. |
| 2017/0252149 A1 | 9/2017 | Kudo et al. |
| 2017/0252150 A1 | 9/2017 | Kudo et al. |
| 2017/0258582 A1 | 9/2017 | Kudo et al. |
| 2017/0354493 A1 | 12/2017 | Andersen et al. |
| 2018/0250125 A1 | 9/2018 | Kudo |
| 2019/0151078 A1 | 5/2019 | Watanabe et al. |
| 2019/0192284 A1 | 6/2019 | Watanabe et al. |
| 2020/0113674 A1 | 4/2020 | Someya et al. |

FOREIGN PATENT DOCUMENTS

| | | |
|---|---|---|
| DE | 19544119 A1 | 5/1997 |
| EP | 0363213 | 4/1990 |
| EP | 0727966 | 9/2003 |
| EP | 1360947 A1 | 11/2003 |
| EP | 1832247 A1 | 9/2007 |
| EP | 1338254 | 12/2008 |
| EP | 2074961 A1 | 7/2009 |
| EP | 2255751 A1 | 12/2010 |
| EP | 2286763 A1 | 2/2011 |
| EP | 2286764 A1 | 2/2011 |
| EP | 2574308 A2 | 4/2013 |
| EP | 2853236 A2 | 4/2015 |
| FR | 2749752 A | 12/1997 |
| JP | 63-197453 A | 8/1988 |
| JP | 4-212350 A | 8/1992 |
| JP | 5-103808 | 4/1993 |
| JP | 5-103809 | 4/1993 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-325569 A | 11/2003 |
| JP | 2003-325570 A | 11/2003 |
| JP | 2003-325572 A | 11/2003 |
| JP | 2004-024854 A | 1/2004 |
| JP | 2004-188194 A | 7/2004 |
| JP | 2004-351196 A | 12/2004 |
| JP | 2006-181269 A | 7/2006 |
| JP | 2006-297146 A | 11/2006 |
| JP | 2006-333924 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-244570 A | 9/2007 |
| JP | 2007-526091 A | 9/2007 |
| JP | 2007-307168 A1 | 11/2007 |
| JP | 2008-521535 A | 6/2008 |
| JP | 2008-212689 A | 9/2008 |
| JP | 2014-050484 A | 3/2014 |
| JP | 2016-137122 A | 8/2016 |
| WO | WO9407436 A1 | 4/1994 |
| WO | WO9513022 A1 | 5/1995 |
| WO | WO9628122 A1 | 9/1996 |
| WO | WO9715253 A1 | 5/1997 |
| WO | WO9812969 A1 | 4/1998 |
| WO | WO9958086 A1 | 11/1999 |
| WO | WO9959668 A1 | 11/1999 |
| WO | WO0045746 A1 | 8/2000 |
| WO | WO0062712 A1 | 10/2000 |
| WO | WO2002071982 A1 | 9/2002 |
| WO | WO2002096322 A1 | 12/2002 |
| WO | WO2005023154 A1 | 3/2005 |
| WO | WO2005070341 A1 | 8/2005 |
| WO | WO2005084588 A1 | 9/2005 |
| WO | WO2006070628 A1 | 7/2006 |
| WO | WO2006080191 A1 | 8/2006 |
| WO | WO2006090531 A1 | 8/2006 |
| WO | WO2007037223 A1 | 4/2007 |
| WO | WO2007097221 A1 | 4/2007 |
| WO | WO2007080869 A1 | 7/2007 |
| WO | WO2008149794 A1 | 12/2008 |
| WO | WO2008149795 A1 | 12/2008 |
| WO | WO2009058929 A1 | 7/2009 |
| WO | WO2009148091 A1 | 12/2009 |
| WO | WO2011126144 A1 | 10/2011 |
| WO | WO2011155636 A1 | 12/2011 |
| WO | WO2012086797 A1 | 6/2012 |
| WO | WO2012155887 A1 | 11/2012 |
| WO | WO2015012312 A1 | 1/2015 |

OTHER PUBLICATIONS

U.S. Appl. No. 15/476,717, filed Mar. 31, 2017, US 20170202662A1.
U.S. Appl. No. 15/888,078, filed Feb. 4, 2018.
U.S. Appl. No. 15/382,377, filed Dec. 16, 2016, US 20170151056A1.
U.S. Appl. No. 15/071,880, filed Mar. 16, 2016, US 20160193038A1.
U.S. Appl. No. 15/870,979, filed Jan. 14, 2018.
U.S. Appl. No. 15/126,277, filed Sep. 14, 2016, US 20170079772A1.
U.S. Appl. No. 15/756,565, filed Feb. 28, 2018.
U.S. Appl. No. 15/756,569, filed Feb. 28, 2018.
PCT Search Report dated Dec. 13, 2016 for PCT App. Ser. No. PCT/JP2016/077328.
U.S. Appl. No. 16/550,144, filed Aug. 23, 2019.
EPO Extended European Search Report dated May 14, 2019 for EPO App. Ser. No. 16846586.2.
U.S. Appl. No. 16/313,180, filed Dec. 26, 2018.
U.S. Appl. No. 12/602,442, filed Dec. 15, 2009, U.S. Pat. No. 8,747,465.
U.S. Appl. No. 13/244,449, filed Sep. 24, 2011, U.S. Pat. No. 9,289,288.
U.S. Appl. No. 15/063,395, filed Mar. 7, 2016, U.S. Pat. No. 10,390,940.
U.S. Appl. No. 15/476,717, filed Mar. 31, 2017, U.S. Pat. No. 10,405,971.
U.S. Appl. No. 16/550,144, filed Aug. 23, 2019, US 20200113674A1.
U.S. Appl. No. 12/602,454, filed Dec. 15, 2009, U.S. Pat. No. 8,475,528.
U.S. Appl. No. 13/244,452, filed Sep. 24, 2011, U.S. Pat. No. 8,535,375.
U.S. Appl. No. 12/667,510, filed Dec. 31, 2009, U.S. Pat. No. 9,114,006.
U.S. Appl. No. 14/812,104, filed Jul. 29, 2015, U.S. Pat. No. 9,907,647.
U.S. Appl. No. 12/995,263, filed Dec. 15, 2010, U.S. Pat. No. 9,554,894.
U.S. Appl. No. 15/382,377, filed Dec. 16, 2016, U.S. Pat. No. 10,517,717.
U.S. Appl. No. 12/997,651, filed Dec. 13, 2010, U.S. Pat. No. 8,382,769.

(56) References Cited

OTHER PUBLICATIONS

U.S. Appl. No. 13/757,790, filed Feb. 2, 2012, U.S. Pat. No. 9,186,246.
U.S. Appl. No. 13/583,216, filed Apr. 6, 2011, U.S. Pat. No. 9,326,847.
U.S. Appl. No. 13/699,708, filed Jun. 8, 2011, U.S. Pat. No. 8,647,382.
U.S. Appl. No. 14/145,846, filed Dec. 31, 2013, U.S. Pat. No. 9,314,373.
U.S. Appl. No. 15/071,880, filed Mar. 16, 2016, U.S. Pat. No. 10,039,668.
U.S. Appl. No. 15/336,678, filed Oct. 27, 2016, U.S. Pat. No. 9,572,710.
U.S. Appl. No. 15/608,895, filed May 30, 2017, U.S. Pat. No. 9,980,811.
U.S. Appl. No. 13/059,401, filed Feb. 16, 2011, U.S. Pat. No. 8,702,795.
U.S. Appl. No. 13/061,143, filed Feb. 26, 2011, U.S. Pat. No. 8,470,032.
U.S. Appl. No. 13/143,322, filed Jul. 5, 2011, U.S. Pat. No. 8,603,103.
U.S. Appl. No. 14/099,989, filed Dec. 8, 2013, U.S. Pat. No. 9,655,718.
U.S. Appl. No. 15/600,679, filed May 19, 2017, U.S. Pat. No. 9,877,826.
U.S. Appl. No. 15/600,684, filed May 19, 2017, U.S. Pat. No. 9,901,442.
U.S. Appl. No. 11/814,508, filed Jul. 23, 2007, U.S. Pat. No. 8,545,512.
U.S. Appl. No. 14/033,888, filed Sep. 23, 2013, U.S. Pat. No. 9,220,593.
U.S. Appl. No. 11/816,676, filed Aug. 20, 2007, U.S. Pat. No. 8,523,877.
U.S. Appl. No. 13/966,209, filed Aug. 13, 2013, U.S. Pat. No. 9,364,320.
U.S. Appl. No. 12/095,172, filed May 28, 2008, U.S. Pat. No. 8,523,941.
U.S. Appl. No. 14/011,018, filed Aug. 27, 2013, U.S. Pat. No. 8,968,328.
U.S. Appl. No. 12/088,328, filed Mar. 27, 2008, U.S. Pat. No. 8,574,239.
U.S. Appl. No. 14/065,365, filed Oct. 28, 2013, U.S. Pat. No. 9,114,007.
U.S. Appl. No. 11/722,601, filed Apr. 10, 2008, U.S. Pat. No. 8,460,311.
U.S. Appl. No. 15/126,277, filed Sep. 14, 2016, U.S. Pat. No. 10,383,723.
U.S. Appl. No. 15/756,565, filed Feb. 28, 2018, US 20180250125A1.
U.S. Appl. No. 15/756,569, filed Feb. 28, 2018, US 20180353287A1.
U.S. Appl. No. 16/313,180, filed Dec. 26, 2018, US 20190192284A1.
U.S. Appl. No. 16/313,184, filed Dec. 26, 2018, US 20190151078A1.

* cited by examiner

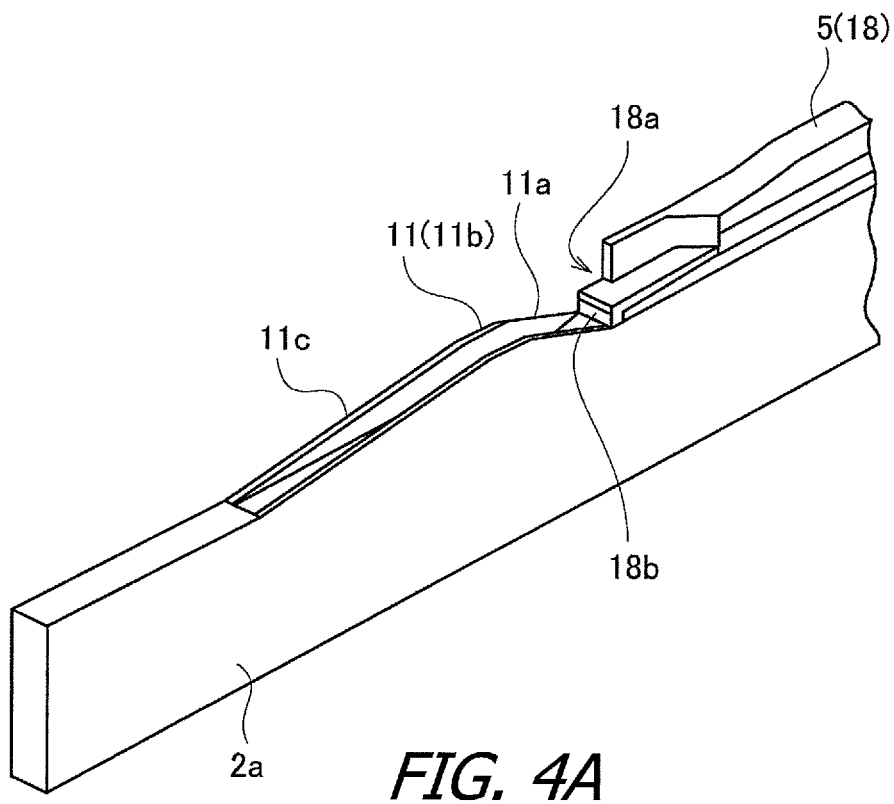
FIG. 4A
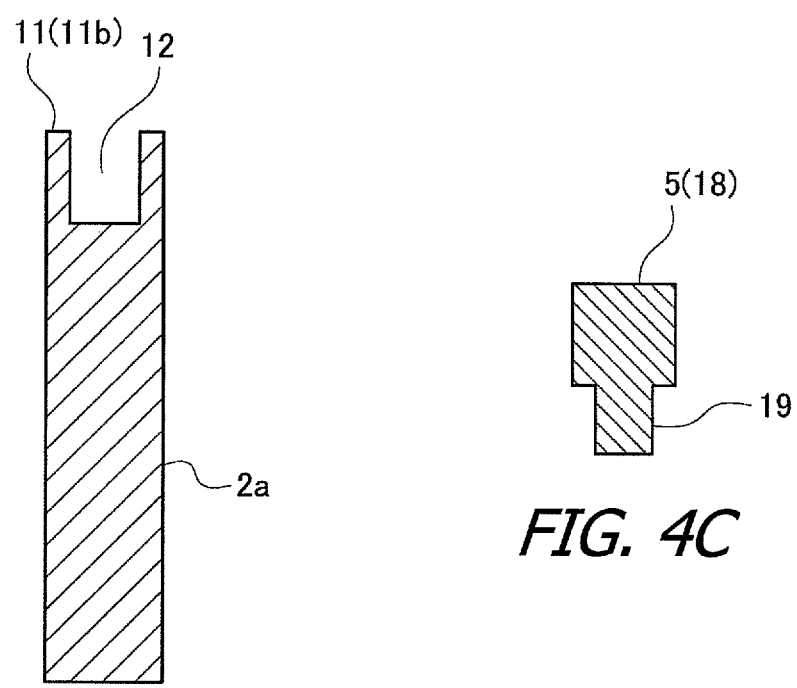
FIG. 4B
FIG. 4C

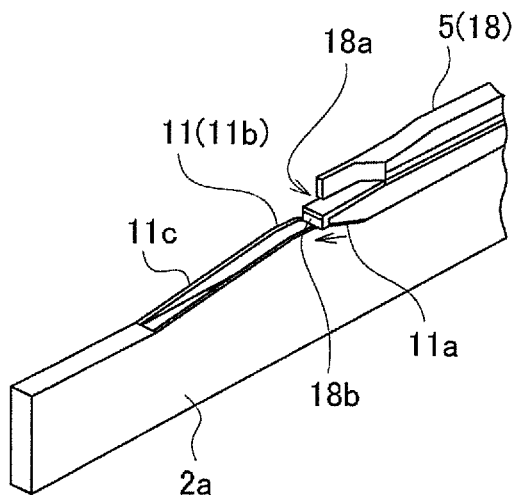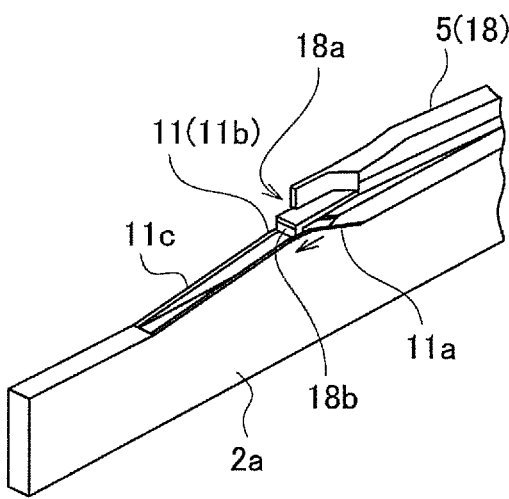
FIG. 6A          FIG. 6B
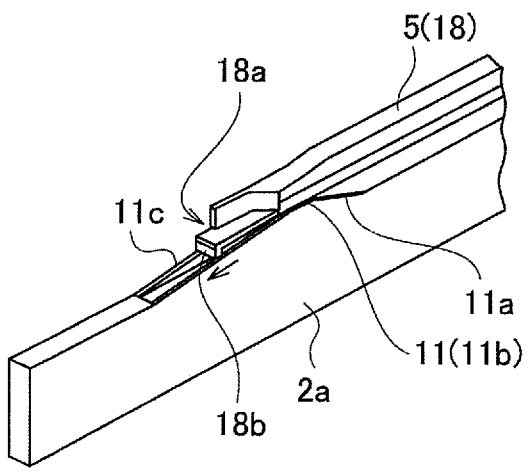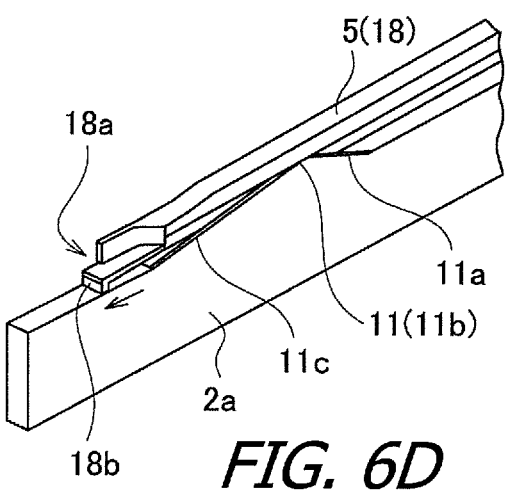
FIG. 6C          FIG. 6D

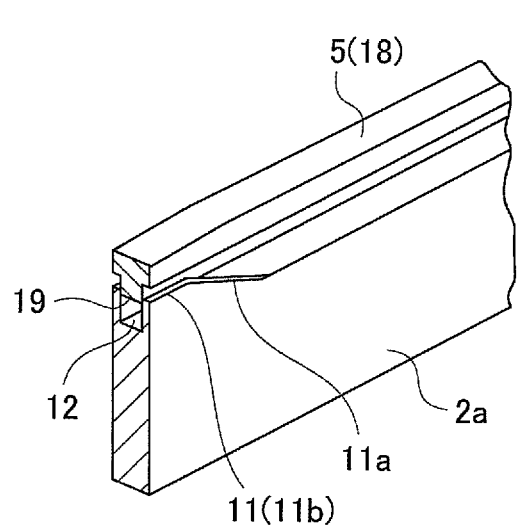 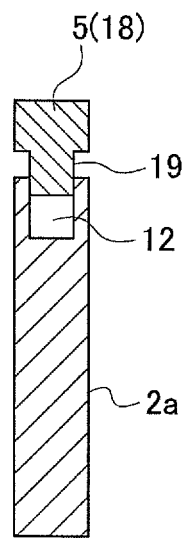
FIG. 7A    FIG. 7B
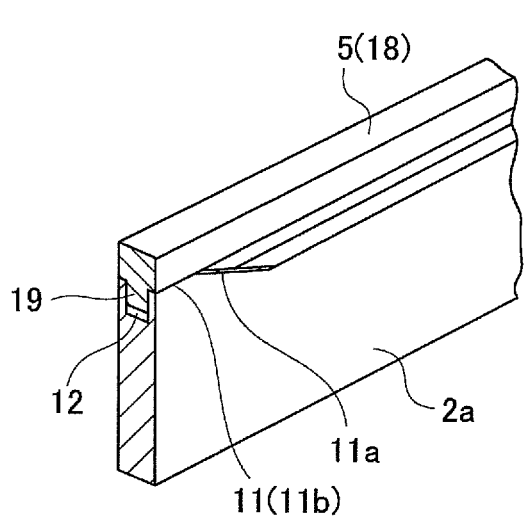 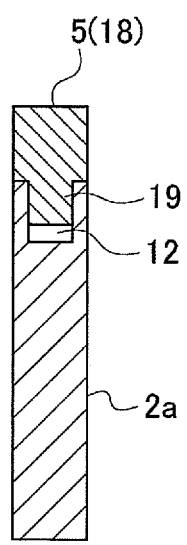
FIG. 8A    FIG. 8B

INTRAOCULAR LENS INJECTOR

TECHNICAL FIELD

The present invention relates to an intraocular lens injector used for injecting an intraocular lens into an eye.

DESCRIPTION OF RELATED ART

As one of a cataract surgery, it is widely practiced to extract a white cloudy lens by ultrasonic emulsification and suction and then inject the intraocular lens into the eye. Further, in recent years, in order to realize minimally invasive cataract surgery with less burden on an eye, a one-piece type intraocular lens made of a soft material such as silicone elastomer or soft acrylic is injected into the eye in a small folded state. The one-piece type intraocular lens has an optical portion that performs a lens function and a pair of support portions that extend from the optical portion, and an entire intraocular lens is made of a flexible material.

Further, as an intraocular lens injector for handling the one-piece type intraocular lens, there is an injector having a function of folding an intraocular lens so as to embrace a pair of support portions with an optical portion in order to improve operability for a surgeon to inject the intraocular lens as much as possible (for example, see patent document 1). In this type of intraocular lens injector, it is necessary to fold the optical portion roundly in a state that tip end parts of the respective support portions are set on a surface of the optical portion. Further, conventional intraocular lens injectors include the one having a pushing member which pushes out an intraocular lens and which folds the intraocular lens when the intraocular lens is pushed out by the pushing member.

PRIOR ART DOCUMENT

Patent Document

[Patent Document 1] Japanese Unexamined Patent Publication No. 2011-255029

SUMMARY OF THE INVENTION

Problem to be Solved by the Invention

However, the conventional intraocular lens injector involves a problem that when the intraocular lens is pushed out by the pushing member, the tip end part of the support portion is caught in an edge of the optical portion or the like, and the tip end part of the support portion is not set smoothly on the surface of the optical portion.

A main object of the present invention is to provide an intraocular lens injector capable of surely placing the tip end part of the support portion on the surface of the optical portion when the intraocular lens is folded so as to embrace the support portion with the optical portion.

Means for Solving the Problem

According to a first aspect, there is provided an intraocular lens injector configured to inject an intraocular lens having an optical portion and a pair of support portions extending from the optical portion into an eye, including:
an injector main body having a lens setting portion on which the intraocular lens is set;
a holding portion that holds a tip end part of a front support portion of the pair of support portions, which is disposed in front of the lens setting portion; and
a displacement mechanism for displacing the optical portion relatively downward with respect to the front support portion held by the holding portion.

According to a second aspect, there is provided the intraocular lens injector of the first aspect, including:
a pushing member that pushes out the intraocular lens from the lens setting portion by moving in a direction of a central axis of the injector main body, and
the displacement mechanism including a guide mechanism that guides the optical portion so as to pass under the holding portion when the pushing member pushes out the intraocular lens.

According to a third aspect, there is provided the intraocular lens injector of the second aspect, wherein the holding portion has a housing portion for detachably housing a tip end part of the front support portion, and is configured so that the tip end part of the front support portion is disengaged from the housing portion when the optical portion passes under the holding portion by being pushed by the pushing member.

According to a fourth aspect of the present invention, there is provided the intraocular lens injector of the second aspect, wherein the guide mechanism includes a first guide portion formed on a lower surface of the holding portion in a state of being inclined with respect to a horizontal surface, and a second guide portion formed in a state of being inclined in the same direction as the first guide portion at a position facing the first guide portion.

According to a fifth aspect of the present invention, there is provided the intraocular lens injector of the fourth aspect, wherein the pushing member has a rod portion that pushes out the intraocular lens while being displaced downward along the inclination of the second guide portion.

According to a sixth aspect of the present invention, there is provided the intraocular lens injector of any one of the first to fifth aspects, which is a pre-load type in which the intraocular lens is preset on the lens setting portion.

According to a seventh aspect of the present invention, there is provided the intraocular lens injector of any one of the first to sixth aspects, wherein the intraocular lens is set on the lens setting portion in a no-load state.

Advantage of the Invention

According to the present invention, when folding the intraocular lens so as to embrace the support portions with the optical portion, the tip end part of the support portions can be securely set on the surface of the optical portion.

BRIEF DESCRIPTION OF THE DRAWINGS

FIG. 4A is a perspective view for describing a shape of a protruding guide formed in a moving direction of a rod portion, FIG. 4B is a view showing a cross-sectional shape at the top portion of the protruding guide, and FIG. 4C is a view showing a cross-sectional shape of the rod portion passing through the protruding guide.

FIGS. 6A to 6D are views showing time-sequentially a state in which the tip end part of the rod portion is displaced in the vertical direction in conformity with the shape of the protruding guide.

FIG. 7A is a perspective view showing a cross-sectional shape at the top portion of the protruding guide, and FIG. 7B is a front view thereof.

FIG. 8A is a perspective view showing a cross-sectional shape of a top portion of a protruding guide, and FIG. 8B is a front view thereof.

DETAILED DESCRIPTION OF THE INVENTION

Figure 1:
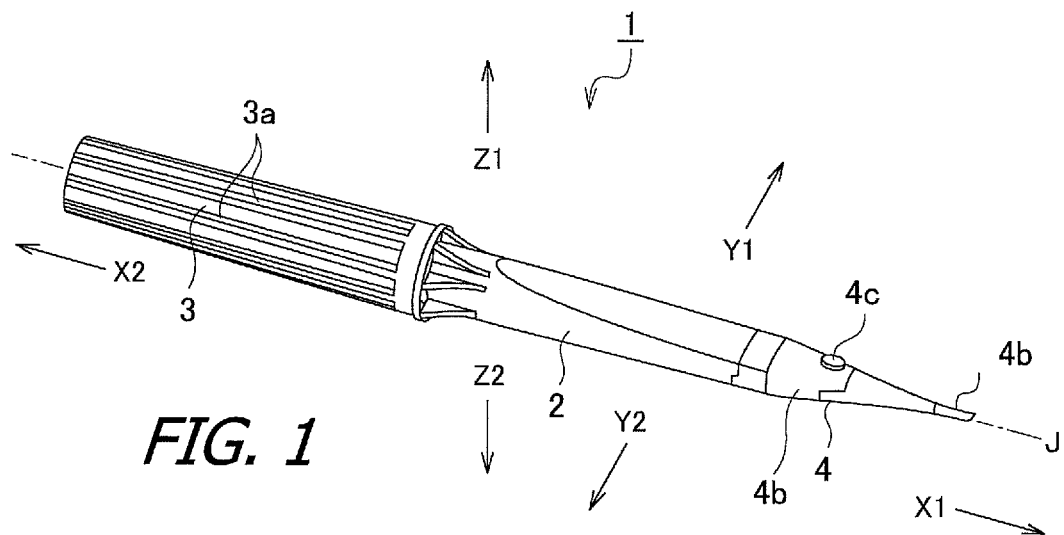
FIG. 1 is a perspective view showing an overall structure of an intraocular lens injector according to an embodiment of the present invention.
Figure 2:
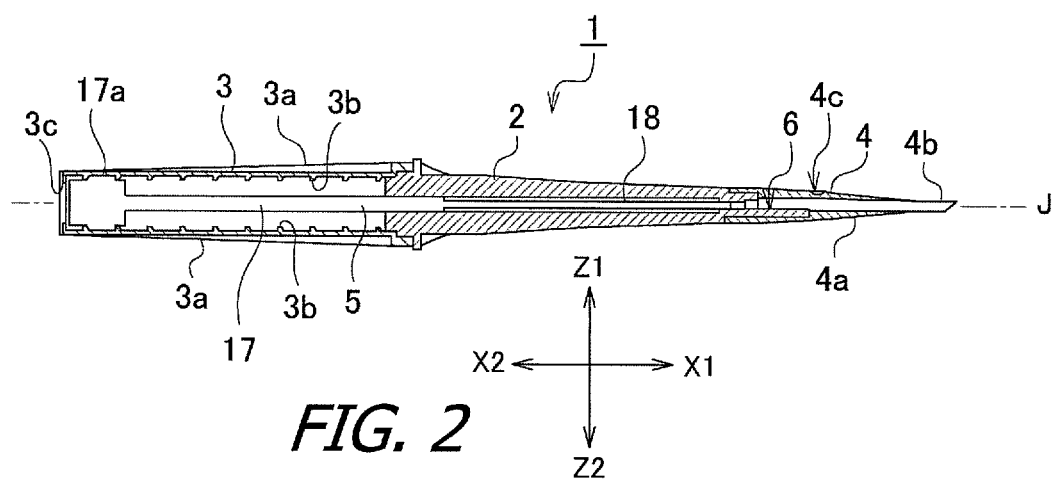
FIG. 2 is a side sectional view showing the overall structure of the intraocular lens injector according to an embodiment of the present invention.
Figure 3A:
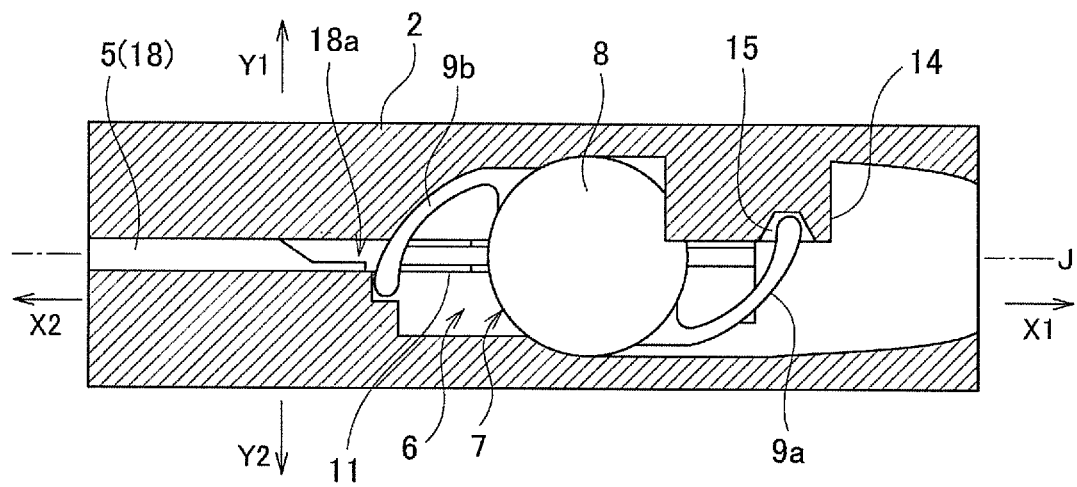
FIG. 3A is a plan sectional view showing a structure of an essential part of an intraocular lens injector according to an embodiment of the present invention.
Figure 3B:
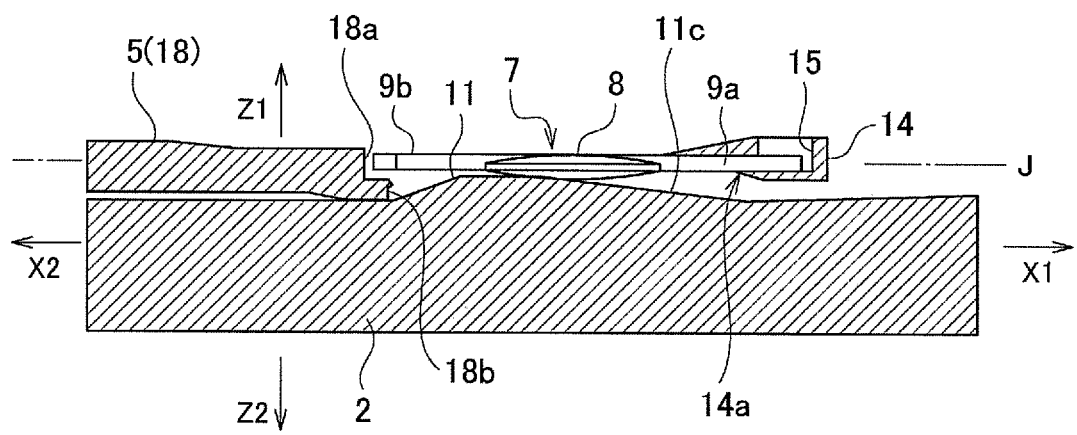
FIG. 3B is a side sectional view showing this essential part structure.

Embodiments of the present invention will be described hereafter in detail, with reference to the drawings. In the embodiment of the present invention, explanation will be given in the following order.
1. Structure of an intraocular lens injector
2. Method for assembling the intraocular lens injector
3. Operation of the intraocular lens injector
4. Effect of the embodiment
5. Modified example, etc.
1. Structure of an Intraocular Lens Injector FIG. 1 is a perspective view showing an overall structure of an intraocular lens injector according to an embodiment of the present invention, and FIG. 2 is a side sectional view showing the overall structure of the intraocular lens injector according to an embodiment of the present invention. Further, FIG. 3A is a plan sectional view showing a structure of an essential part of an intraocular lens injector according to an embodiment of the present invention, and FIG. 3B is a side sectional view showing this essential part structure.

An intraocular lens injector 1 shown in the figure is provided as a disposable product, and is used when injecting the intraocular lens into the eye. The intraocular lens injector 1 roughly includes an injector main body 2, an operation portion 3, an injection tube 4, and a pushing member 5. Each part of the intraocular lens injector 1 is made of resin. The intraocular lens injector 1 is of a preload type in which an intraocular lens is preset. In the preload type intraocular lens injector 1, the intraocular lens is preset on the lens setting portion described later in the stage of shipping the intraocular lens injector 1 from a factory.

In this embodiment, in order to clarify a relative positional relationship and a direction of movement and the like of each part of the intraocular lens injector 1, X1 direction is set as a tip end side (front side), X2 direction is set as a rear end side (rear side), Y1 direction is set as a left side (left side), Y2 direction is set as a right side (right side), Z1 direction is set as an upper side (upper side), and Z2 direction is set as a lower side (lower side). Among them, the X1 direction and the X2 direction correspond to a direction of a central axis of the intraocular lens injector 1 (hereinafter also referred to simply as a "central axis direction"), and the Y1 direction and the Y2 direction correspond to a width direction (left-right direction) of the intraocular lens injector 1, and the Z1 direction and the Z2 direction correspond to a height direction (vertical direction) of the intraocular lens injector 1. Further, a plane parallel to the X1 direction, the X2 direction, the Y1 direction and the Y2 direction is set as a horizontal plane, and a plane perpendicular to the horizontal plane is set as a vertical plane. Reference symbol J in the figure indicates the central axis of the intraocular lens injector 1.

Injector Main Body

The injector main body 2 is formed in a tubular shape as a whole. A hollow portion that allows the movement of the pushing member 5 in the X1 direction and the X2 direction is formed inside of the injector main body 2. A lens setting portion 6 is provided at a tip end part of the injector main body 2. The lens setting portion 6 is formed so as to protrude forward from an outer circumferential wall on a lower side of the injector main body 2. The intraocular lens 7 is set on the lens setting portion 6. A central axis J of the intraocular lens injector 1 coincides with each central axis of the injector main body 2, the operation part 3, and the injection tube 4.

In this embodiment, as an example, one-piece type intraocular lens 7 made of a soft material such as silicone elastomer or soft acrylic is to be handled. The intraocular lens 7 has an optical portion 8 that performs an optical function and a pair (two) support portions 9a, 9b extending outwardly from the outer peripheral edge of the optical portion 8 in an arc shape. The optical portion 8 is formed in a circular shape in plan view. Each of the pair of support portions 9a, 9b is formed in an elongated arm shape. In FIG. 2, the notation of the intraocular lens 7 is omitted.

Here, a structure of the lens setting portion 6 will be described in detail with reference to FIGS. 3A to 4C.

A protruding guide 11 is formed on the lens setting portion 6. The protruding guide 11 is formed in a trapezoidal shape (mountain shape) in a side view in a state in which a part of the lens setting portion 6 is protruded upward. FIG. 4B is a sectional view of a place where the protruding guide 11 is formed when viewed from the central axis direction (front). As can be seen from this figure, a recessed groove 12 is formed on the place where the protruding guide 11 is formed. The protruding guide 11 includes an upward inclined portion 11a, a non-inclined top portion 11b, and a downward inclined portion 11c with a gentler slope than the inclined portion 11a. As shown in FIG. 4A, the protruding guide 11 is an upward inclined portion 11a in the beginning from the rear end side to the tip end side of the intraocular lens injector 1, and after passing through the top portion 11b, it becomes a gentle downward inclined portion 11c. A depth of the groove 12 becomes the deepest at the top portion 11b of the protruding guide 11, and the abovementioned FIG. 4B shows the cross-section of the top portion 11b.

Reference numeral 2a in FIGS. 4A and 4B shows a part of the injector main body 2 virtually cut out, and a part of the injector main body 2 is not shaped as shown in the figure. This point is the same for FIGS. 6A to 8B.

Further, a pair of right and left recessed grooves (not shown) are formed in the lens setting portion 6. The pair of recessed grooves are formed on the left and right side walls defining the lens setting portion 6 of the injector main body 2 so as to face each other. When the intraocular lens 7 is set on the lens setting portion 6, the pair of recessed grooves are engaged with a part of the outer peripheral edge of the optical portion 8, thereby restricting the vertical movement of the optical portion 8.

The holding portion 14 is formed in a state of partially protruding a left side wall portion of the left and right side wall portions partitioning the lens setting portion 6. A part of the lower surface of the holding portion 14 is an inclined surface 14*a* (see FIG. 3B). The inclined surface 14*a* of the holding portion 14 is formed on a lower surface of the holding portion 14 as an example of a "first guide portion". In contrast, the abovementioned downward inclined portion 11*c* of the protruding guide 11 is formed on the lens setting portion 6 as an example of a "second guide portion". The first guide portion and the second guide portion described here, constitutes a guide mechanism for guiding the optical portion 8 so as to pass under the holding portion 14 when the intraocular lens 7 set on the lens setting portion 6 is pushed out by the pushing member 5.

The inclined surface 14*a* is formed to be inclined with respect to the horizontal plane. Specifically, the inclined surface 14*a* is inclined so that a front side is lower than a rear side of the inclined surface 14*a* with respect to the horizontal surface. Further, the inclined surface 14*a* is disposed to face the inclined portion 11*c* of the protruding guide 11 in a vertical direction. The inclined surface 14*a* and the inclined portion 11*c* are inclined in the same direction.

Further, a housing portion 15 is formed in the holding portion 14. The housing portion 15 detachably houses the tip end part of the support portion 9*a* when the intraocular lens 7 is set on the lens setting portion 6. The housing portion 15 is formed in a recessed shape in a state of opening upward and rightward at a right end part of the upper surface of the holding portion 14.

Further, on the tip end side of the lens setting portion 6, an opposing distance between the left and right side wall portions defining the lens setting portion 6 is gradually narrowed, for delivering the optical portion 8 of the intraocular lens 7 to the injection tube 4 in a state of being slightly rounded by the left and right side wall portions.

The intraocular lens 7 is set on the lens setting portion 6 having the abovementioned structure, in a state in which one of the support portions 9*a* is disposed in front of the lens setting portion 6 and the other support portion 9*b* is disposed behind the lens setting portion 6. Therefore, one support portion 9*a* corresponds to a "front support portion" and the other support portion 9*b* corresponds to a "rear support portion". Further, in the lens setting portion 6, the optical portion 8 of the intraocular lens 7 is set (placed) substantially horizontally on the top portion 11*b* of the protruding guide 11.

Further, as shown in FIG. 3A, in a state in which the intraocular lens 7 is set on the lens setting portion 6, a part of the holding portion 14 and a part of the optical portion 8 overlap in a planar manner. Specifically, a part of the outer peripheral part of the optical portion 8 overlaps on the inclined surface 14*a* of the holding portion 14. Further, in a state in which the intraocular lens 7 is set on the lens setting portion 6, the movement of the support portion 9*a* in the central axis direction and the movement of the support portion 9*a* toward the front and rear are respectively restricted by housing the tip end part of the support portion 9*a* in the housing portion 15 of the holding portion 14.

Operation Portion

The operation portion 3 is coaxially connected to the rear end part of the injector main body 2. In this connected state, the operation portion 3 is supported so as to be rotatable around the central axis of the injector main body 2. The operation portion 3 is formed into a tubular shape. A plurality of protrusions 3*a* are formed on the outer peripheral surface of the operation portion 3. Each protrusion 3*a* is formed in parallel to a longitudinal direction of the operation portion 3. The operation portion 3 is a portion rotated by a user such as an operator when the intraocular lens 7 is pushed out using the pushing member 5. At this time, by forming a plurality of protrusions 3*a* on the outer periphery of the operation portion 3, the fingers of the user are caught in the protrusions 3*a*, and therefore it is easy to rotate the operation portion 3.

As shown in FIG. 2, a first screw portion 3*b* is formed on the inner peripheral surface of the operation portion 3. The first screw portion 3*b* constitutes a female screw. The first screw portion 3*b* is formed substantially throughout the central axis direction of the operation portion 3. An abutting portion 3*c* is formed at a rear end part of the operation portion 3. The abutting portion 3*c* is formed by bending inward so as to narrow an opening diameter of the rear end part of the operation portion 3. The abutting portion 3*c* is a portion where the rear end part of a plunger portion 17 abuts so that the plunger portion 17 does not protrude rearward from the rear end part of the operation portion 3.

Injection Tube

An injection tube 4 functions to guide the intraocular lens 7 set on the lens setting portion 6 into an eye in a state that the intraocular lens 7 is folded into a small size when the intraocular lens 7 is injected into the eye. The injection tube 4 integrally has a hollow injection tube main body 4*a* and a narrow tubular nozzle portion 4*b*. The injection tube 4 is attached to a tip end part of the injector main body 2. In this attachment state, the lens setting portion 6 of the injector main body 2 is housed in the injection tube main body 4*a* of the injection tube 4.

An injection portion 4*c* is formed on an upper wall of the insertion tube main body 4*a*. The injection portion 4*c* is provided for injecting a viscoelastic substance (for example, sodium hyaluronate etc.). The viscoelastic substance injected from the injection portion 4*c* is discharged to the vicinity of the intraocular lens 7 set on the lens setting portion 6, thereby supplying the viscoelastic substance to the intraocular lens 7. The injection of the viscoelastic substance is performed before pushing out the intraocular lens 7 by the pushing member 5.

The diameter of the tip end side of the injection tube main body 4*a* is gradually decreased. The nozzle portion 4*b* is formed at the tip end part of the injection tube 4. The tip end part of the nozzle portion 4*b* opens with an oblique incision. Therefore, the opening of the nozzle portion 4*b* faces obliquely downward. The tip end part of the nozzle portion 4*b* is a portion to be inserted into an incisional wound of the eyeball when the intraocular lens 7 is injected into the eye using the intraocular lens injector 1.

Pushing Member

The pushing member 5 is provided movably in the central axis direction of the injector main body 2. The pushing member 5 functions to push out the intraocular lens 7 form the lens setting portion 6 by moving in the central axis direction of the injector main body 2. At this time, the pushing member 5 moves in the hollow portion formed by the injector main body 2, the operation portion 3, and the injection tube 4.

The pushing member 5 has the plunger portion 17 and a rod portion 18. The plunger portion 17 and the rod portion 18 may constitute the pushing member 5 in a unitary structure, or the plunger portion 17 and the rod portion 18 may have separate structures and they may be mutually assembled to constitute the pushing member 5. The plunger portion 17 is disposed relatively rearwardly, and the rod portion 18 is disposed relatively forward in the direction of the central axis of the intraocular lens injector 1.

The plunger portion 17 is formed into a rod shape. In the initial state before use, the plunger portion 17 is disposed in a state of being inserted into the operation portion 3 so as not to protrude from the rear end part of the operation portion 3. A second screw portion 17a is formed at the rear end part of the plunger portion 17. The second screw portion 17a constitutes a male screw. The second screw portion 17a is engaged with the first screw portion 3b inside of the operation portion 3. When the intraocular lens injector 1 is used, the operation portion 3 is operated so as to rotate around the central axis of the injector main body 2, thereby moving the entire pushing member 5 in a forward direction. A movement start position of the plunger portion 17 at that time is uniquely determined by abutting the rear end part of the plunger portion 17 against the abutting portion 3c of the operation portion 3.

The rod portion 18 is provided for folding the intraocular lens 7 into a predetermined shape by pushing out the intraocular lens 7 forward which is set on the lens setting portion 6, and in this state, releasing the intraocular lens 7 from the opening of the nozzle portion 4b of the injection tube 4. The rod portion 18 is formed in a rod shape thinner than the plunger portion 17. The rod portion 18 is configured to be elastically deformable so as to have moderate flexibility. A first contact portion 18a and a second contact portion 18b are formed at the tip end part of the rod portion 18. When the intraocular lens 7 is pushed out by the rod portion 18, the first contact portion 18a comes into contact with the support portion 9b and the second contact portion 18b comes into contact with the optical portion 8. The upper end portion of the second contact portion 18b protrudes like a canopy so as to grip the edge of the optical portion 8. On the lower surface of the rod portion 18, a protrusion 19 is formed as shown in FIG. 4C. The protrusion 19 is formed on a place closer to a rear end side of the rod portion 18 than the place where the first contact portion 18a and the second contact portion 18b are formed, so as to avoid this place, in a longitudinal direction of the rod portion 18.

2. Method for Assembling the Intraocular Lens Injector

Next, a method for assembling the intraocular lens injector 1 will be described.

First, after preparing the members (2, 3, 4, 5) constituting the intraocular lens injector 1, the pushing member 5 is attached to the operation portion 3. Specifically, the tip end opening part of the operation portion 3 is engaged with the rear end part of the plunger portion 17 of the pushing member 5 so as to cover this opening part, so that the operation portion 3 is rotated. Thereby, the first screw portion 3b formed on the inner peripheral surface of the operation portion 3 and the second screw portion 17a provided at the rear end part of the plunger portion 17 are engaged with each other. Therefore, when the operation portion 3 is rotated while restricting the rotation of the pushing member 5, the plunger portion 17 is inserted into the operation portion 3 in accordance with the rotation of the operation portion 3. At this time, the operation portion 3 is rotated until the rear end part of the plunger portion 17 abuts against the abutting portion 3c of the operation portion 3.

Next, the injector main body 2 is attached to the operation portion 3. At this time, the rod portion 18 of the pushing member 5 is inserted into the hollow portion of the injector main body 2. Thereby, the tip end parts (18a, 18b) of the rod portion 18 are disposed slightly in front of the lens setting portion 6.

Next, the separately prepared intraocular lens 7 is set on the lens setting portion 6 of the injector main body 2. At this time, the optical portion 8 of the intraocular lens 7 is placed substantially horizontally on the top portion 11b of the protruding guide 11. Further, one support portion 9a is disposed in front of the lens setting portion 6, where the tip end part of the supporting portion 9a is housed in the housing portion 15 of the holding portion 14.

In the state in which the intraocular lens 7 is set on the lens setting portion 6 as described above, the intraocular lens 7 is set in a no-load state. The no-load state refers to a state in which almost no load (pressure) is applied to the intraocular lens, that is, a state in which the intraocular lens maintains its original shape. The original shape of the intraocular lens refers to the shape in the stage of finishing manufacturing the intraocular lens.

Next, the injection tube 4 is attached to the tip end part of the injector main body 2. Thus, the assembly of the intraocular lens injector 1 incorporating the intraocular lens 7 is completed. For the structure for connecting the injector main body 2 and the operation portion 3 and the structure for connecting the injector main body 2 and the injection tube 4, for example, the structure described in the specification of Japanese Patent Application No. 2014-55761 and drawings (Japanese Patent Application Laid-open No. 2015-177845) may be adopted, or any other connecting structure may be adopted.

3. Operation of the Intraocular Lens Injector

Next, the operation of the intraocular lens injector 1 will be described.

Movement of the Pushing Member

First, the operation of the pushing member 5 will be described when the operation portion 3 is rotated.

When the operation portion 3 is rotated in one direction, the pushing member 5 moves forward by the engagement between the first screw portion 3b and the second screw portion 17a. At this time, the plunger portion 17 of the pushing member 5 moves straight in the central axis direction of the injector main body 2 while engaging with the hollow portion of the injector main body 2. Further, the pushing member 5 moves as shown in FIGS. 5A to 5D in accordance with the rotation operation of the operation portion 3.

Figure 5A:
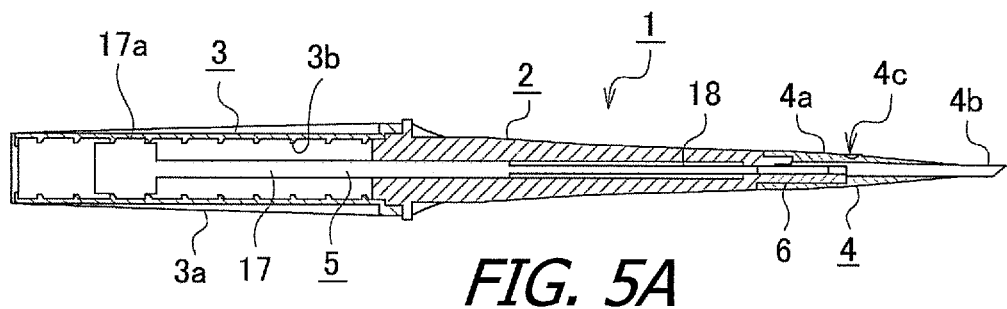
FIGS. 5A to 5D are views showing time-sequentially a state of a movement of a pushing member in accordance with a rotation operation of the operation portion.
Figure 5B:
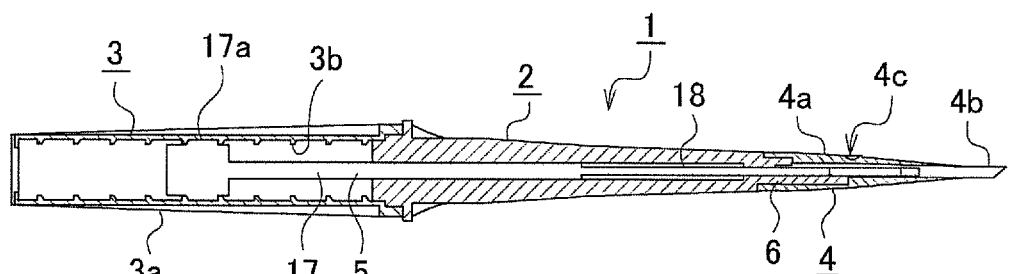
Figure 5C:
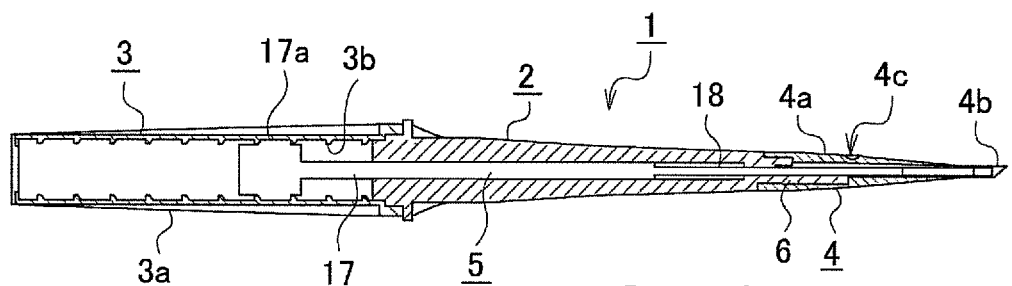
Figure 5D:
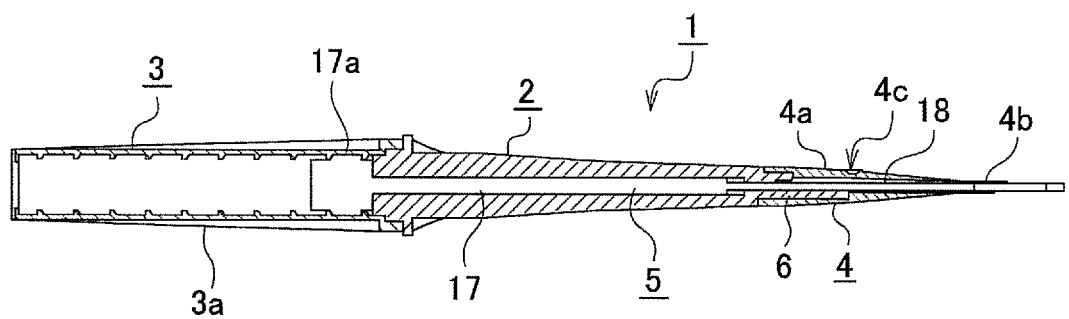

FIG. 5A shows a stage in which the tip end part of the rod portion 18 of the pushing member 5 is advanced to the tip end part of the lens setting portion 6, and FIG. 5B shows a stage in which the tip end part of the rod portion 18 is advanced to the injection tube main body 4a of the injection tube 4. Further, FIG. 5C shows a stage in which the tip end part of the rod portion 18 is advanced to the nozzle portion 4b of the injection tube 4, and FIG. 5D shows a stage in which the tip end part of the rod portion 18 protrudes forward from the nozzle portion 4b of the injection tube 4.

Movement of the Tip of the Rod Portion

When the pushing member 5 is moved as described above, the tip end part of the rod portion 18 of the pushing member 5 is vertically displaced in conformity with the shape of the protruding guide 11, due to elastic deformation of the rod portion 18 itself. This state will be described with reference to FIGS. FIGS. 6A to 6D.

First, when the pushing member 5 starts to move forward in accordance with the rotation operation of the operating portion 3, as shown in FIG. 6A, the tip end parts (parts indicated by reference numerals 18a and 18b) of the rod portion 18 are displaced upward along the upward inclined portion 11a of the protruding guide 11. Next, the tip end part of the rod portion 18 reaches the top portion 11b of the protruding guide 11 as shown in FIG. 6B.

Next, as shown in FIG. 6C, the tip end part of the rod portion 18 is displaced downward in accordance with the downward inclined portion 11c of the protruding guide 11. At this time, the sectional shape at the top portion 11b of the protruding guide 11 is as shown in FIGS. 7A and 7B. Namely, after the tip end part of the rod portion 18 has passed through the top portion 11b of the protruding guide 11, a part of the protrusion 19 formed on the lower surface of the rod portion 18 enters the groove 12 of the protruding guide 11. Thereby, the tip end part of the rod portion 18 can be displaced downward according to the downward inclined portion 11c of the protruding guide 11.

Next, as shown in FIG. 6D, the tip end part of the rod portion 18 moves forward after moving downward along the inclined portion 11c of the protruding guide 11. At this time, the sectional shape at the top portion 11b of the protruding guide 11 is as shown in FIGS. 8A to 8D. Namely, after the tip end part of the rod portion 18 has passed through the inclined portion 11c of the protruding guide 11, all of the protrusions 19 formed on the lower surface of the rod portion 18 enter the groove 12 of the protruding guide 11. Thereby, the tip end part of the rod portion 18 can be advanced forward by avoiding the interference between the protruding guide 11 and the rod portion 18.

Movement of Intraocular Lens

Further, when the pushing member 5 is moved as described above, the intraocular lens 7 set on the lens setting portion 6 is pushed forward by the rod portion 18 of the pushing member 5. Such a state will be described, using plan views of FIGS. 9A to 9D, a side sectional view of FIGS. 10A to 10D, and a perspective view of FIGS. 11A to 11D.

Figure 9A:
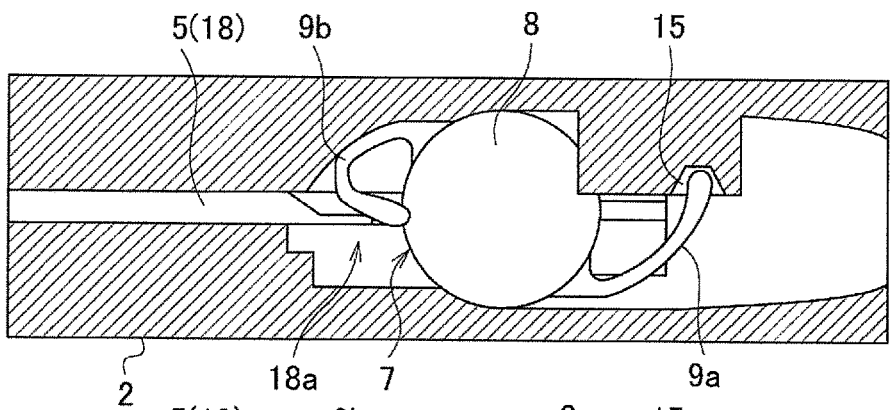
FIGS. 9A to 9D are plan sectional views time-sequentially showing the movement of the intraocular lens pushed out by the pushing member.
Figure 10A:
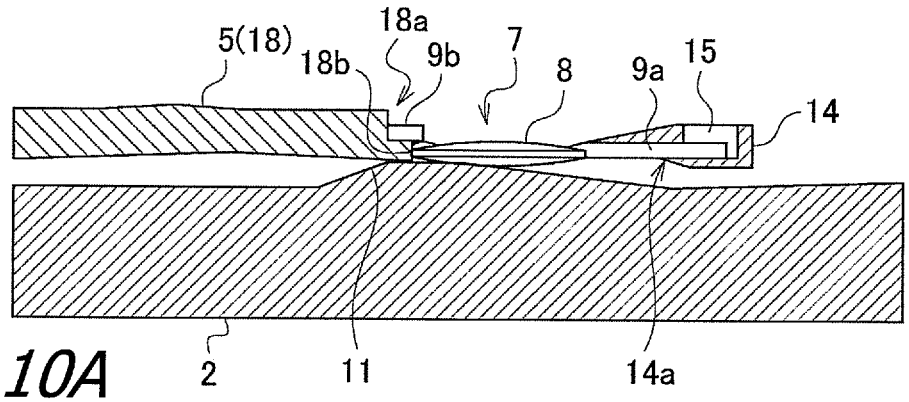
FIGS. 10A to 10D are side sectional views time-sequentially showing a state in which the intraocular lens is pushed out by the pushing member.
Figure 11A:
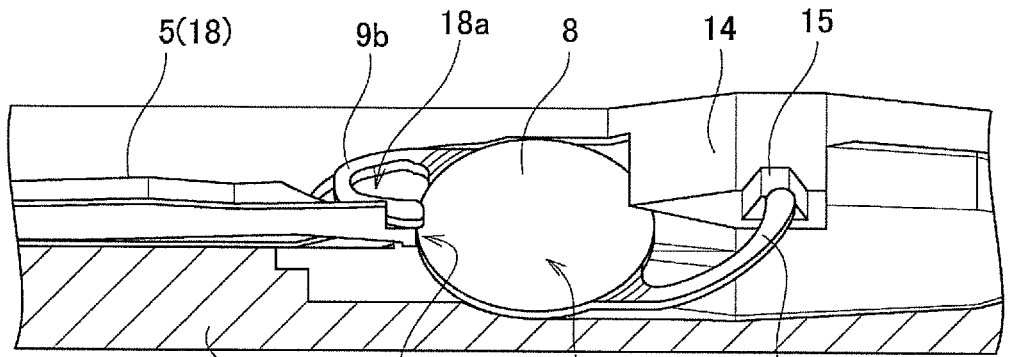
FIGS. 11A to 11D are perspective views time-sequentially showing the movement of the intraocular lens pushed out by the pushing member.

First, when the pushing member 5 starts moving forward in accordance with the rotation operation of the operation portion 3, the tip end part of the rod portion 18 comes into contact with the support portion 9b and subsequently the optical portion 8 (see FIGS. 9A, 10A and 11A). Specifically, the first contact portion 18a of the rod portion 18 comes into contact with the support portion 9b first and then the second contact portion 18b of the rod portion 18 comes into contact with the optical portion 8.

At this time, the first contact portion 18a of the rod portion 18 pushes the support portion 9b forward while keeping in contact with the support portion 9b, thereby bending the entire support portion 9b toward the optical portion 8 in a substantially U-shape. Further, the tip end part of the support portion 9b rides on the first contact portion 18a and in this state the tip end part of the rod portion 18 is displaced upward along the upward inclined portion 11a of the protrusion guide 11. Then, when the tip end part of the rod portion 18 reaches the top portion 11b of the protruding guide 11, the second contact portion 18b comes into contact with the edge of the optical portion 8. Further, the tip end part of the support portion 9b rides on the surface of the optical portion 8.

Figure 9B:
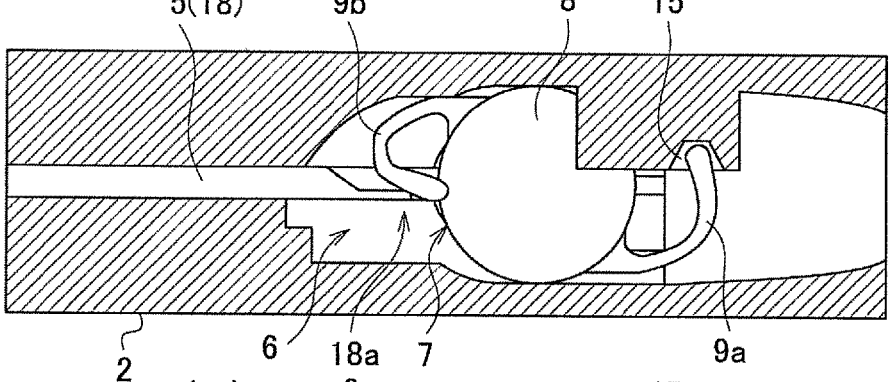
Figure 10B:
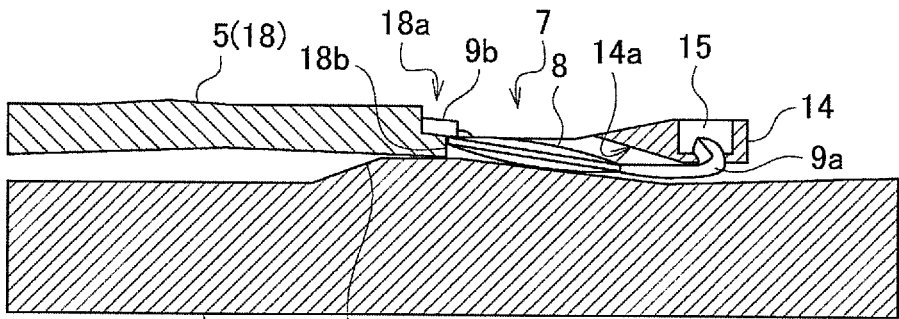
Figure 11B:
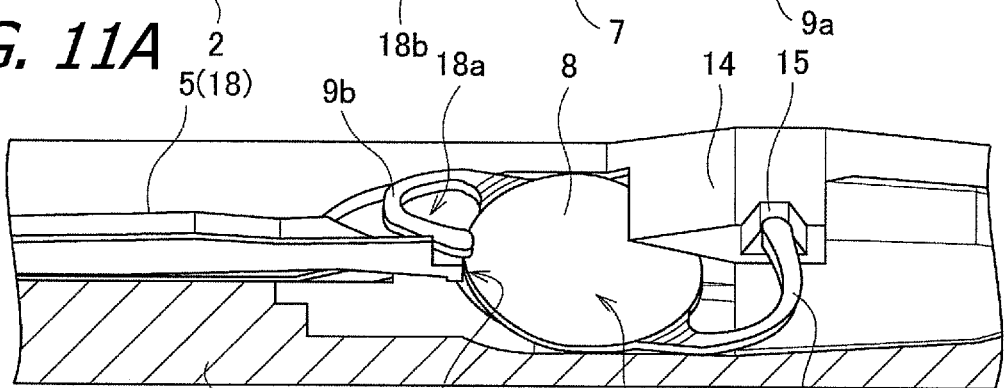

Next, the tip end part of the rod portion 18 pushes the entire intraocular lens 7 forward while coming into contact with the support portion 9b and the optical portion 8 (see FIGS. 9B, 10B and 11B). At this time, the tip end part of the rod portion 18 advances along the top portion 11b of the protruding guide 11 while gripping the edge of the optical portion 8 using the second contact portion 18b. Thereby, the optical portion 8 of the intraocular lens 7 is pushed out from the top portion 11b of the protruding guide 11 to the inclined portion 11c. The optical portion 8 thus pushed out is tilted obliquely along the inclined portion 11c on the downward side of the protruding guide 11.

Meanwhile, the entire support portion 9a is bent by the movement of the optical portion 8 while the tip end part of the support portion 9a is housed in the housing portion 15 of the holding portion 14. The reason why the support portion 9a is bent in this way is as follows.

First, the tip end part of the support portion 9a is restricted from moving forward by being housed in the housing portion 15 of the holding portion 14. Therefore, even if the optical portion 8 is pushed by the rod portion 18 and moves forward, the tip end part of the support portion 9a is caught in the housing portion 15 and is fixed thereto. Accordingly, when the optical portion 8 is pushed forward at the tip end part of the rod portion 18, a force in a direction opposite to the pushing direction is applied to the support portion 9a. Therefore, the support portion 9a is gradually bent according to the movement of the optical portion 8.

Figure 9C:
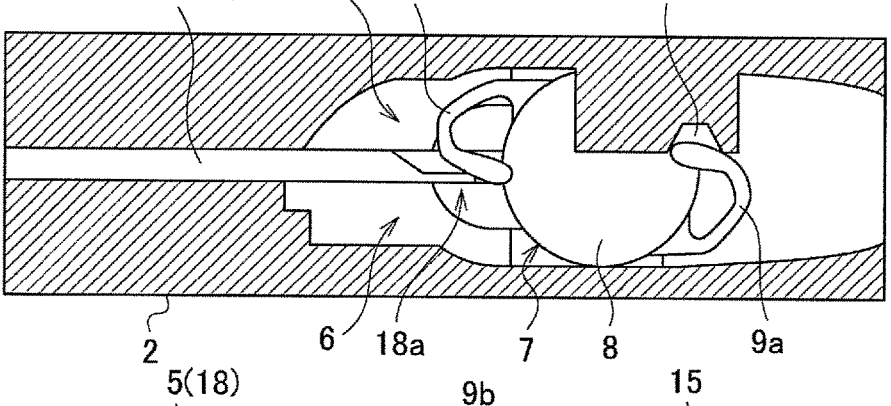
Figure 10C:
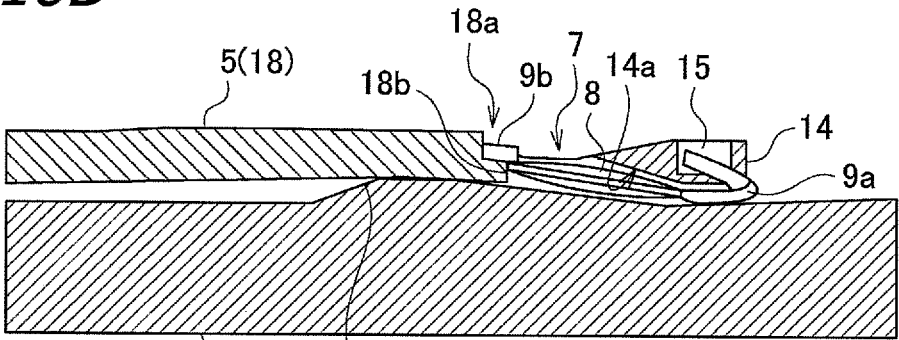
Figure 11C:
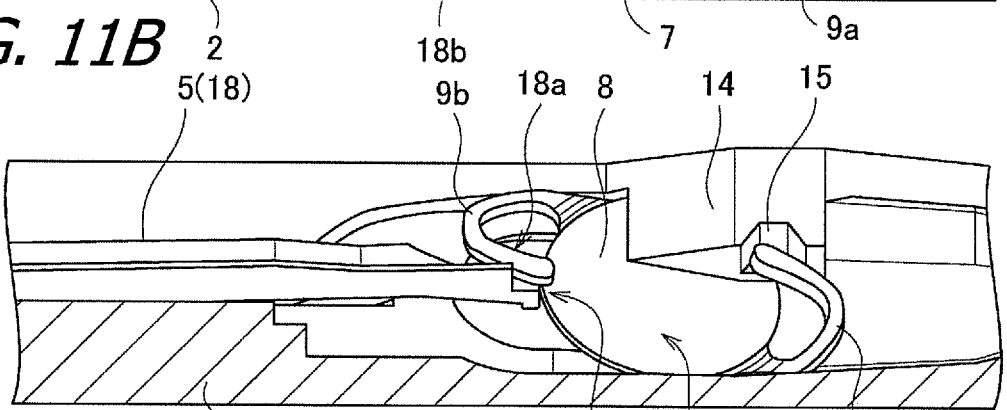

Next, the tip end part of the rod portion 18 pushes the entire intraocular lens 7 further forward while coming contact with both the support portion 9b and the optical portion 8 (see FIGS. 9C, 10C and 11C). At this time, the tip end part of the rod portion 18 is displaced downward along the inclined portion 11c of the protruding guide 11 while gripping the edge of the optical portion 8 using the second contact portion 18b. Then, the optical portion 8 moves obliquely downward while being guided by the downward inclined portion 11c of the protruding guide 11 and the inclined surface 14a of the holding portion 14 opposed thereto. Meanwhile, the support portion 9a is bent to a greater extent by the movement of the optical portion 8 while its tip end part is caught in the housing portion 15 of the holding portion 14. Specifically, the entire support portion 9a is bent toward the optical portion 8 so as to form a substantially U-shape. At this time, due to the oblique downward movement of the optical portion 8 described above, the position of the optical portion 8 relative to the position of the support section 9a is relatively displaced downward.

Figure 9D:
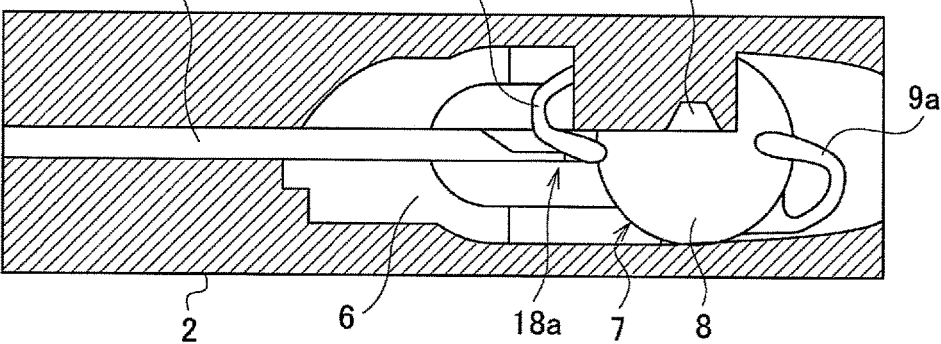
Figure 10D:
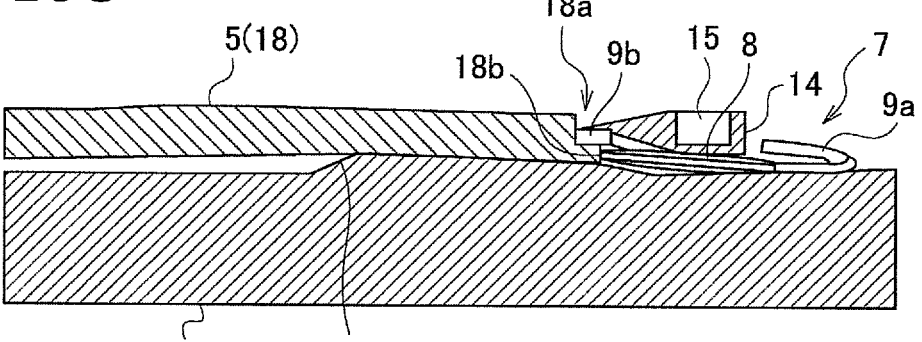
Figure 11D:
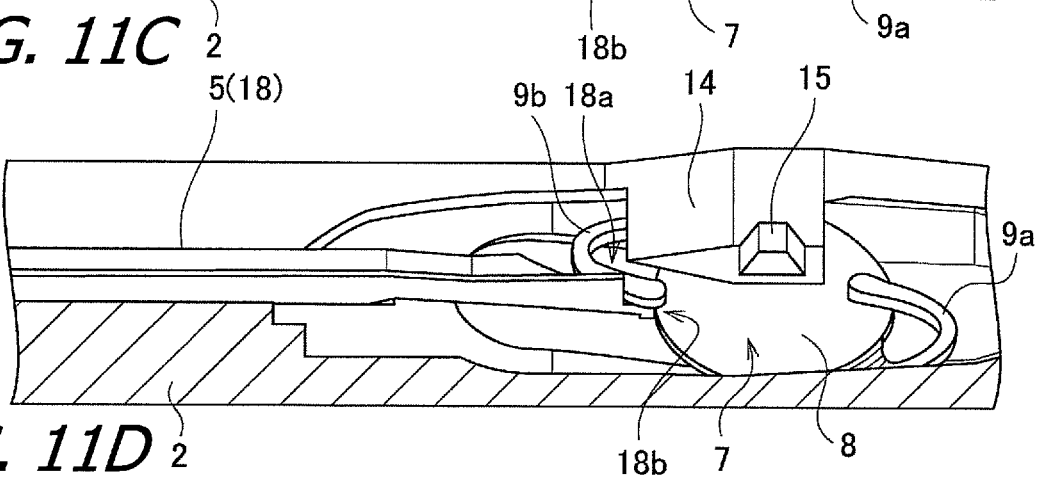

Next, when the optical portion 8 passes under the holding portion 14 by the pushing operation of the rod portion 18, the tip end part of the support portion 9a is detached from the housing portion 15 of the holding portion 14 (see FIGS. 9D, 10D and 11D). At this time, the tip end part of the support portion 9a detached from the housing portion 15 rides on the surface of the optical portion 8 which is passing under the holding portion 14. Further, the optical portion 8 with the tip end part of the support portion 9a ridden thereon, is gradually deformed by being pushed by the left and right side wall portions of the lens setting portion 6, and a base end side portion of the support portion 9a also comes into contact with one side wall portion of the lens setting portion 6. Thereby, shape restoration of the support portion 9a is suppressed. Therefore, the support portion 9a is maintained in the state of being bent in a substantially U-shape without returning to an original shape, and the tip end part of the support portion 9a is kept on the surface of the optical portion 8.

Thereafter, the intraocular lens 7 is pushed out into the injection tube 4 by the movement of the rod portion 18. At that time, the optical portion 8 of the intraocular lens 7 is rounded from the left and right by the inner wall of the injection tube main body 4a having a tapered shape, and is finally folded so as to embrace the pair of support portions 9a, 9b. The intraocular lens 7 thus folded is pushed out from the nozzle portion 4b of the injection tube 4 by the rod portion 18. At this time, the intraocular lens 7 can be injected into the eye by pushing out the intraocular lens 7 from the opening of the nozzle portion 4*b* in a state in which the nozzle portion 4*b* of the injection tube 4 is inserted into the incisional wound of the eyeball.

4. Effect of the Embodiment

According to an embodiment of the present invention, one or more effects described below are obtained.

(1) In the embodiment of the present invention, the tip end part of the support portion 9*a* of the intraocular lens 7 set on the lens setting portion 6 of the injector main body 2 is held by the holding portion 14, and a displacement mechanism for relatively displacing the optical portion 8 downward with respect to the support portion 9*a*. Therefore, the tip end part of the support portion 9*a* can be securely placed on the surface of the optical portion 8.

(2) In the embodiment of the present invention, a guide mechanism (11*c*, 14*a*) is provided for guiding the optical portion 8 so as to pass under the holding portion 14 when the intraocular lens 7 is pushed out from the lens setting portion 6 by the pushing member 5. Therefore, the optical portion 8 can be relatively displaced downward using the pushing operation of the pushing member 5.

(3) In the embodiment of the present invention, the housing portion 15 for housing the tip end part of the support portion 9*a* is provided in the holding portion 14, and when the optical portion 8 passes under the holding portion 14 by being pushed by the pushing member 5, the tip end part of the support portion 9*a* is detached from the housing portion 15. Therefore, by using the pushing operation of the pushing member 5, the tip end part of the support portion 9*a* can be detached from the housing portion 15 and placed on the surface of the optical portion 8 while bending the support portion 9*a* toward the optical portion 8.

(4) In the embodiment of the present invention, the preload type intraocular lens injector 1 is adopted, in which the intraocular lens 7 is preset on the lens setting portion 6. Therefore, a user using the intraocular lens injector 1 is not required to perform a setting work of setting the intraocular lens 7 each time. Therefore, it is possible to reduce a burden on the user in cataract surgery.

(5) In the embodiment of the present invention, the intraocular lens 7 is set on the lens setting portion 6 of the injector main body 2 in a no-load state, and therefore, even if the preload type intraocular lens injector 1 incorporating the intraocular lens 7 therein, is stored for a long period of time, the shape of the intraocular lens 7 is not affected. Accordingly, there is no possibility that the restorability of the shape of the intraocular lens 7 to be inserted into the eye is impaired by using the intraocular lens injector 1.

5. Modified Example, Etc.

The technical scope of the present invention is not limited to the embodiments described above but includes various modifications and improvements within the scope of deriving specific effects obtained by the constituent features of the invention and combinations thereof.

For example, in the abovementioned each embodiment, the preload type intraocular lens injector 1 is given as an example. However, the present invention is not limited thereto, and the present invention may be applied to an intraocular lens injector of the type in which the user using the intraocular lens injector sets the intraocular lens each time.

Further, in the abovementioned each embodiment, the pushing member 5 is moved forward by the rotating operation of the operation portion 3. However, the present invention is not limited thereto, and it is also acceptable to adopt a structure in which the pushing member is pushed directly using a finger.

DESCRIPTION OF SIGNS AND NUMERALS

1 Intraocular lens injector
2 Injector main body
3 Operation portion
4 Injection tube
5 Pushing member
6 Lens setting portion
7 Intraocular lens
8 Optical portion
9*a* Support portion (front support portion)
9*b* Support portion (rear support portion)
11 Protruding guide
11*a* Inclined portion
11*b* Top portion
11*c* Inclined portion
14 Holding portion
15 Housing portion
18 Rod portion

The invention claimed is:

1. An intraocular lens injector configured to inject an intraocular lens having an optical portion and a pair of support portions extending from the optical portion into an eye, comprising:
   an injector main body having a lens setting portion on which the intraocular lens is set;
   a holding portion that holds a tip end part of a front support portion of the pair of support portions, which is disposed in front of the lens setting portion; and
   a displacement mechanism for displacing the optical portion relatively downward with respect to the front support portion held by the holding portion;
   wherein the holding portion and the displacement mechanism are respectively configured and positioned relative to one another such that distal movement of the optical portion results in the optical portion moving under the holding portion while the tip end part of the front support portion is held above the optical portion by the holding portion.

2. The intraocular lens injector according to claim 1, further comprising:
   a pushing member that pushes out the intraocular lens from the lens setting portion by moving in a direction of a central axis of the injector main body, and
   wherein the displacement mechanism comprises a guide mechanism that guides the optical portion under the holding portion.

3. The intraocular lens injector according to claim 2, wherein the holding portion has a housing portion for detachably housing a tip end part of the front support portion, and is configured so that the tip end part of the front support portion is detached from the housing portion when the optical portion passes under the holding portion by being pushed by the pushing member.

4. The intraocular lens injector according to claim 2, wherein the guide mechanism includes a first guide portion formed on a lower surface of the holding portion in a state of being inclined with respect to a horizontal surface, and a second guide portion formed in a state of being inclined in the same direction as the first guide portion at a position facing the first guide portion.

5. The intraocular lens injector according to claim 4, wherein the pushing member has a rod portion that pushes out the intraocular lens while being displaced downward along the inclination of the second guide portion.

6. The intraocular lens injector according to claim 1, which is a pre-load type in which the intraocular lens is preset on the lens setting portion.

7. The intraocular lens injector according to claim 1, wherein the intraocular lens is set on the lens setting portion in a no-load state.

8. An intraocular lens injector, comprising: an injector main body having a lens setting portion and a surface and defining a central axis direction and a height direction; a holding portion with a recess located forward of the lens setting portion; an intraocular lens, on the lens setting portion in a no-load state, having an optical portion, a rear support portion with a tip end, and a front support portion with a tip end that is located within the holding portion recess; and a displacement mechanism configured to simultaneously displace the optical portion along the surface in the central axis direction and in the height direction relative to the front support portion, while the tip end part of the front support portion is within the holding portion recess, such that the optical portion is located between the surface and the holding portion.

9. The intraocular lens injector according to claim 8, further comprising:
a pushing member that pushes the intraocular lens from the lens setting portion by moving in the central axis direction.

10. The intraocular lens injector according to claim 9, wherein the displacement mechanism comprises a guide mechanism that guides the optical portion under the holding portion.

11. The intraocular lens injector according to claim 10, wherein the holding portion is configured such that the tip end part of the front support portion exits the recess when the optical portion passes under the holding portion.

12. The intraocular lens injector according to claim 10, wherein the guide mechanism includes a first inclined guide portion on a lower surface of the holding portion and a second inclined guide portion that faces the first inclined guide portion.

13. The intraocular lens injector according to claim 12, wherein the pushing member includes a rod portion that pushes the intraocular lens while being displaced in the central axis direction and in the height direction along the second inclined guide portion.

\* \* \* \* \*